United States Patent
Böhm et al.

(10) Patent No.: US 7,122,010 B2
(45) Date of Patent: Oct. 17, 2006

(54) METHOD AND APPARATUS FOR DETERMINING ALVEOLAR OPENING AND CLOSING

(75) Inventors: Stephan Böhm, 22, D-20251, Hamburg-Eppendorf (DE); Marcelo B. P. Amato, Respiratory ICU-Pulmonary Dept., Hospital das Clinicas, Faculdada de Medicina da Universidade de Sao Paulo, 155, 2nd Floor, Bloco 11, Rua Eneas Carvalho de Aguiar, CEP-05403-900, Sao Paolo (BR); Peter W. A. Kunst, Haarlem (NL)

(73) Assignees: Stephan Bohm, Hamburg-Eppendorf (DE); Marcelo B. P. Amato, Sao Paolo (BR)

( * ) Notice: Subject to any disclaimer, the term of this patent is extended or adjusted under 35 U.S.C. 154(b) by 0 days.

(21) Appl. No.: 10/426,961

(22) Filed: May 1, 2003

(65) Prior Publication Data

US 2004/0073130 A1    Apr. 15, 2004

Related U.S. Application Data

(63) Continuation of application No. 09/875,262, filed on Jun. 7, 2001, now abandoned, which is a continuation of application No. PCT/EP99/09699, filed on Dec. 9, 1999.

(30) Foreign Application Priority Data

Dec. 10, 1998    (DE) .............................. 198 57 090

(51) Int. Cl.
*A61B 5/08*    (2006.01)
*A61M 16/00*    (2006.01)

(52) U.S. Cl. ...................... 600/536; 600/533; 600/534; 128/204.23; 128/204.26

(58) Field of Classification Search ........... 128/204.18, 128/204.21, 204.23, 204.26; 600/413, 533, 600/534, 536
See application file for complete search history.

(56) References Cited

U.S. PATENT DOCUMENTS

| | | | | |
|---|---|---|---|---|
| 3,621,833 A | * | 11/1971 | Crane | 600/533 |
| 4,035,222 A | * | 7/1977 | Amberg | 156/423 |
| 4,617,939 A | * | 10/1986 | Brown et al. | 600/547 |
| 4,630,614 A | * | 12/1986 | Atlas | 600/534 |
| 4,796,639 A | * | 1/1989 | Snow et al. | 600/532 |
| 5,318,038 A | * | 6/1994 | Jackson et al. | 600/533 |
| 5,522,397 A | * | 6/1996 | Vermaak | 600/533 |
| 5,660,170 A | * | 8/1997 | Rajan et al. | 128/204.18 |
| 5,752,509 A | * | 5/1998 | Lachmann et al. | 128/204.23 |
| 5,857,459 A | * | 1/1999 | Snow et al. | 128/204.21 |
| 6,116,241 A | * | 9/2000 | Huygen et al. | 128/204.23 |

FOREIGN PATENT DOCUMENTS

| | | | |
|---|---|---|---|
| EP | 1000580 A1 | * | 5/2000 |
| JP | 2000139866 A | * | 2/2000 |

* cited by examiner

*Primary Examiner*—Michael J. Hayes
*Assistant Examiner*—Michael G. Mendoza
(74) *Attorney, Agent, or Firm*—Shlesinger, Arkwright & Garvey LLP

(57) ABSTRACT

The invention refers to a method for the regional determination of the alveolar opening and alveolar closing of the lung depending on the respiration pressure, wherein according to the method of electrical impedance tomography, an impedance signal is measured in at least one lung zone depending on the respiration pressure. The alveolar opening or closing of a lung zone is determined, in particular to enable an improved artificial respiration.

24 Claims, 22 Drawing Sheets

Figure 2A:
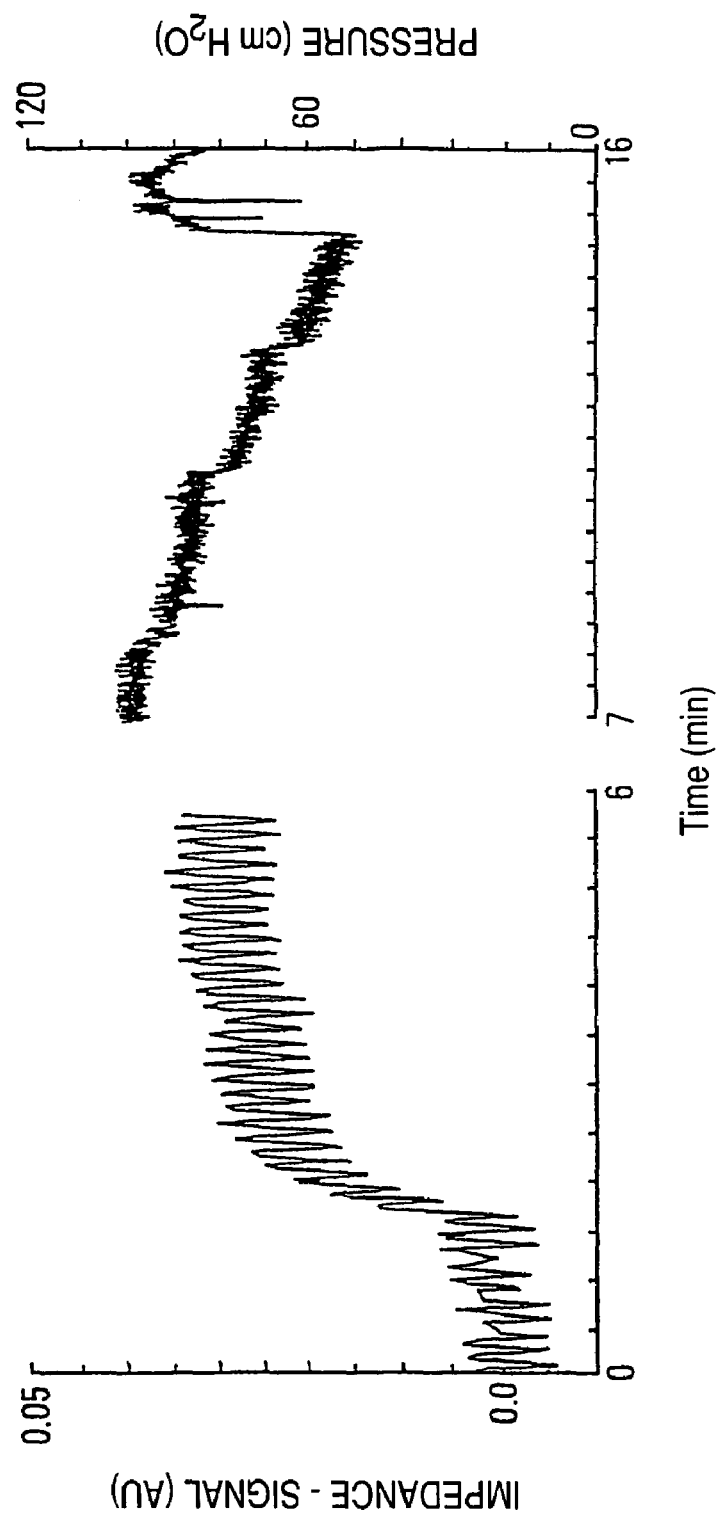

FIG.1
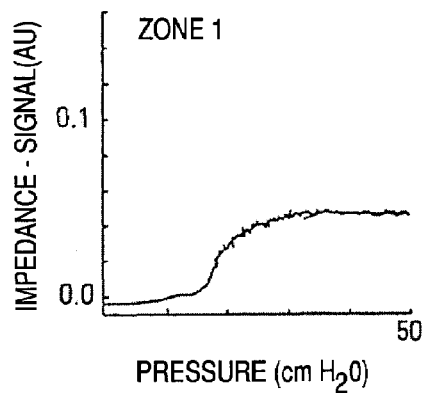
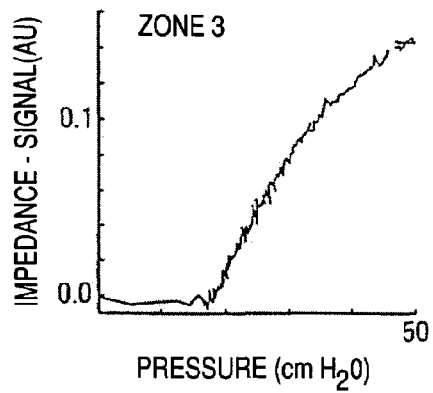
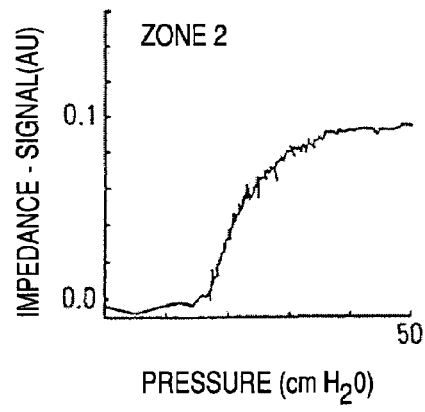
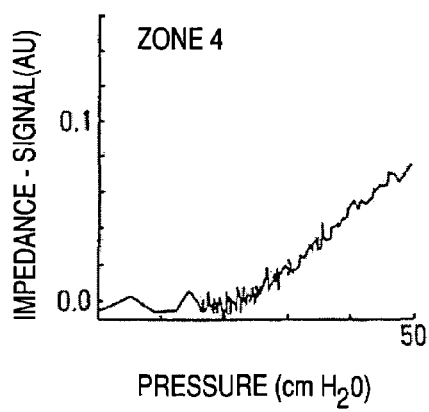

METHOD AND APPARATUS FOR DETERMINING ALVEOLAR OPENING AND CLOSING

RELATED APPLICATIONS

This is a continuation of application Ser. No. 09/875,262, filed Jun. 7, 2001 now abandoned, which is a continuation application of application PCT/EP99/09699, filed Dec. 9, 1999, which claims the priority benefit of German Application No. DE 19857090.2, filed Dec. 10, 1998, which is hereby incorporated by reference.

TECHNICAL FIELD OF THE INVENTION

The invention refers to a method for the determination of the alveolar opening and alveolar closing of the lung depending on the pressure respiration. In particular, the invention enables to a regional determination of the alveolar opening and alveolar closing.

It is known that to measure the lung mechanics, pressure and volume should be recorded and superimposed. If one increases the pressure continuously, as from a certain pressure the first alveoli (terminal lung units or air sacks) begin to change over from the state of collapse into the state of openness. If the pressure is increased further, more and more of the closed alveoli are opened. The maximum number of state changes takes place finally at the turning point of the pressure/volume curve. Thereafter, the opening ebbs away on a further increase in pressure and changes over into saturation, wherein ideally all the alveoli are opened.

One problem in the measurement of the lung mechanics is that the distribution of this opening phenomenon is not homogeneous over the entirety of the lung. For example, the lung is made heavier by the oedema formation, i.e. because of increased accumulation of liquid in the case of inflammations. Thereby a gravity dependent gradient results from the sternum to the spinal column. Thereby above all the lowest parts of the lung are compressed and collapse.

In the case of a traditional pressure-volume measurement, however, one does not receive any information concerning the regional pressure-volume relationship, but one only receives average information on the pressure-volume relationship of the entire lung.

BACKGROUND OF THE INVENTION

For the regional measurement of the pressure-volume relationship the so-called electrical impedance tomography is known. In this process, a number of electrodes are placed around the thorax, wherein an alternating current with e.g. 50 kHz at 5 nA peak to peak amplitude is applied to respectively adjacent electrodes. The other electrodes respectively are used with the alternating current to carry out the measurement of impedance against a defined reference potential. As soon as all the electrodes, one after another, have served as current conducting electrodes, a cycle for data detection is concluded. In order to eliminate statistical disturbances, as a rule a plurality of data detection cycles is averaged, in order to obtain a corresponding picture. The maximal impedance changes in the zone of the thorax are caused by the breathing in and out of air. In this context it can be observed that the impedance change which is measured by electrodes is a measure of the change of volume in the lung. Therefore according to the process of electrical impedance tomography, measurements can also be carried out with respect to the pressure-volume relationship in the lung. However, the special feature of electrical impedance tomography is that on the basis of a computer-based evaluation of the signals at the electrodes, a two-dimensional or even three-dimensional image of the impedance changes can be compiled.

From Dijkstra A. M. et al.: "Review Clinical Applications of Electrical Impedance Tomography", Journal of Medical Engineering & Technology, G B, Basingstoke, Hants, no. 3, May 1993 (1993-05), pages 89–98 a general review of clinical applications of electrical impedance tomography is known. It is shown that besides respiratory applications also applications for the central nervous, cardiovascular and digestive systems are possible.

From Eung Je Woo et al.: "Measuring Lung Resistivity Using Electrical Impedance Tomography", IEEE Transactions on Biomedical Engineering, US, IEEE Inc. New York, vol. 39, no. 7, 1 Jul. 1992 (1992-07-01), pages 756–760 a method for measuring the lung resistivity using electrical impedance tomography is known. It is proposed to use the electrical impedance tomography imaging techniques in the measurement of lung resistivity for the detection and monitoring of apnea and edema.

The artificial respiration of a sick lung, wherein oedemas have formed, is a special problem, because it cannot be exactly controlled whether the lung has already closed and/or collapsed in certain parts. Then it was found that the mortality rate can be reduced substantially when a predetermined pressure is artificially maintained in the lung, which just makes possible keeping open all the alveoli (terminal lung units, air sacks). However, this pressure is not known in the case of artificial respiration, because the alveolar opening and/or closing of the lung could not yet be regionally determined.

Therefore the object of the invention is to make available a method for the determination of the alveolar opening and alveolar closing of the lung, depending on the respiration pressure.

This object is solved by a method comprising the features according to claim 1 and by an apparatus comprising the features according to claim 25. The method according to the invention is based on the cognition that the alveolar opening and/or closing can be determined from an impedance signal gained with the method of electrical impedance tomography. Thereby at least two important values can be determined, namely a first respiration pressure value which corresponds to the alveolar closing of the corresponding lung zone and a second respiration pressure value which corresponds to the alveolar opening of the corresponding lung zone.

Accordingly, the apparatus according to the invention comprises a means for measuring according to the method of electrical impedance tomography an impedance signal (AU) in at least one lung zone depending on the respiration pressure, a means for determining from the impedance signal a first respiration pressure value which corresponds to the alveolar closing of the corresponding lung zone, and a means for determining from the impedance signal a second respiration pressure value which corresponds to the alveolar opening of the corresponding lung zone.

In contrast to computer tomography and magnetic resonance tomography, the process according to the invention can also be carried out at the bed of the patient, because no costly instruments are necessary. In this case there is no radiation stress either for the patient or for the staff. In the case of critical patients constant supervision of the state and degree of openness of the lung can therefore be carried out.

The first effect of the process according to the invention is that the impedance signal is influenced by the breathing movements of the patient. In each breathing movement the lung volume rises and falls. Using the regional impedance curves of electrical impedance tomography it can be observed that the average change of the impedance signal, due to breathing movements, is conspicuously greater in zones wherein the lung has not yet collapsed, whereas in zones wherein the lung has already collapsed, only minor changes in the impedance signal are caused. For example the change in the impedance signal due to breathing movements can be determined on the basis of the unaveraged root mean square of the impedance signal over a plurality of breaths. The change in the impedance signal on the basis of breathing movements is therefore determined from the signal energy of the high frequency portions of the impedance signal, which are based on the breathing movements. But it is equally possible that the change in the impedance signal based on breathing movements can be determined on the basis of an average peak to peak value of the impedance signal over a plurality of breaths.

The alveolar closing and/or opening of the lung or the first and second respiration pressure value respectively is determined on the basis of the change in the impedance signal due to breathing movements, in that the change in the impedance signal based on breathing movements is compared with predetermined breathing movement comparative values. In doing so, it must be taken into account that with respect to the two comparative values, as a rule a certain hysteresis is found. This means that the opening of the pulmonary cells does not take place at the same pressure as the closing of the alveoli (terminal lung units), but that both comparative values fall away from each other. In this context it must in addition be taken into consideration in which direction the respective comparative value passes in order to be able to precisely identify the hysteresis.

With respect to the comparative values it is conceivable that fixed comparative values are predetermined. However, in this case disturbance factors, e.g. based on offset changes, enter fully into the measurement. Therefore it is expedient to determine the breathing movement comparative values dynamically from the average change in the impedance signal on the basis of breathing movements of another zone of the lung. Preferably the lung is divided into a plurality of zone planes perpendicularly to the gravity vector, wherein the other lung zone is a zone which is in the direction of the gravity vector above the lung zone which is concerned. In this case use is made of the fact that as a rule the lung part which is lowest in the direction of the gravity vector is more strongly affected by the pathological appearance of the collapse of the alveoli (terminal lung units) than the correspondingly higher part of the lung zone. Alveolar closing of a lung zone, for example, can be determined as soon as the breathing movement comparative value of the lower lung zone is less by a predetermined factor than the breathing movement comparative value of the lower zone.

A further effect which is suitable to determine the alveolar opening or closing of the lung or the first and second respiration pressure value respectively is the change in the impedance signal due to the collapse of the alveoli. In the case of a pathological lung or an unphysiological condition such as i.e. anaesthesia it is observed that even with constant pressure the lung zone collapses, i.e. the pulmonary units therefore collapse spontaneously. This collapse takes place all the more strongly as the respiration pressure falls, wherein the effect in addition is reinforced like an avalanche over time. Consequently according to the invention alveolar closing of the lung zone or the first respiration pressure value respectively is determined as soon as the average change in the impedance signal due to the collapse of the alveoli falls below a collapse comparative value. Accordingly alveolar opening of a lung zone or the second respiration pressure value respectively is found as soon as the average change in the impedance signal based on the opening of the alveoli is above an opening comparative value.

The average change in the impedance signal due to the collapse of the alveoli, for example, can be determined on the basis of the mean increase in the impedance signal depending on time with a predetermined respiration pressure.

The average increase, for example, can be determined by the Gauβ compensation computation, in that a straight line is placed in a segment of the impedance signal depending on time at constant pressure. The collapse comparative value and/or the opening comparative value can be prescribed as fixed values, or however they can be determined from a dynamic comparative value determination. The dynamic determination of the comparative value is carried out expediently on the basis of an impedance signal in a different lung zone. Preferably the lung is divided, as was described above, into a plurality of zone planes in the direction of the gravity vector, wherein the comparative value is derived from the lung zone which is above the lung zone concerned in the direction of the gravity vector.

A further effect caused by the alveolar opening or closing of a lung zone is the average change of the impedance signal on the basis of respiration pressure changes. As soon as a sudden respiration pressure change is applied to the lung, the impedance signal for this pressure change does not follow at once, but respectively with a certain delay.

Accordingly, alveolar closing or the first respiration pressure value respectively of a lung zone is determined, as soon as the average change in the impedance signal based on respiration pressure changes falls below a first respiration pressure comparative value, and wherein an alveolar opening or the second respiration pressure value respectively of a lung zone is determined as soon as the average change of the impedance signal based on respiration pressure changes moves above a fixed second respiration change comparative value. In this context use is made of the observation that the lung mechanics responds with a certain inertia to changes in pressure. This inertia is larger in the sick zones than in the healthy zones of the lung, because the sick zones only open as from a higher pressure, so that the sick zones can be localised according to the invention.

The change in the impedance signal due to respiration pressure changes, for example, can be determined on the basis of the average initial rise in the impedance signal after a sudden increase in respiration pressure. The initial rise is all the smaller, the more the lung zone which is concerned tends on the basis of pathological changes to a collapse of the terminal lung units or alveoli. Another possibility is that the change of the impedance signal on the basis of respiration pressure changes is determined based on the time constant of the impedance signal, with which the impedance signal follows a change in the respiration pressure. The first respiration pressure comparative value and/or the second respiration pressure comparative value can be prescribed or, however, can be determined dynamically, as was described already above for the other processes. In the case of dynamic determination of the first respiration pressure comparative value and/or of the second respiration pressure comparative value, the determination is carried out on the basis of the average change of the impedance signal due to respiration pressure changes in another lung zone. The other lung zone is again preferably a zone which is in the direction of the gravity vector above the lung zone concerned. In this process the lung is subdivided for the measurement into a plurality of zone planes in the direction of the gravity vector.

According to a preferred embodiment it is provided that setting out from a respiration pressure wherein the lung alveoli are opened in almost all the lung zones, the respiration pressure is reduced step by step, until an alveolar closing of a lung zone is found in one lung zone.

Apart from the division of the lung into zones in the direction of the gravity vector, it is also conceivable that the lung is divided into a plurality of radial sectors, wherein the centre point axis of the sectors is in the direction of the gravity vector.

A device for carrying out the method according to the invention consists of a plurality of electrodes which are applied around the thorax, of an electrical impedance tomograph for the control of individual electrodes and for the evaluation of the impedance signals at the uncontrolled electrodes, in order to obtain a regional impedance signal in the thorax, and of a processing unit to evaluate the regional impedance signals for determining the first respiration pressure value and the second respiration pressure value. Falsification of the signals is to be determined in this context, in particular, due to breathing movements, because on each intake or outlet of breath, the positions of the electrodes in relation to each other alter. In order to eliminate the resultant signal falsifications at the electrodes, a sensor is provided to measure the changing periphery of the thorax caused by the breathing movements. In addition, the electric impedance tomograph comprises a correction unit, wherein the change of impedance signals of the electrodes caused by breathing movements is corrected by including the sensor signal.

An important aspect of the apparatus according to the invention is to control an artificial respiration unit. This can be particularly useful for a sick lung because it cannot be exactly controlled whether the lung has already closed and/or collapsed in certain parts. However, according to the invention it was found that the mortality rate can be reduced substantially when a predetermined pressure is artificially maintained in the lung, which just makes it possible to keep open all the alveoli. This can be done by providing a control unit which is connected to the artificial respiration unit and the processing unit, whereby the first respiration pressure value and the second respiration pressure value is fed from the processing unit to the control unit to control the artificial respiration.

The signals obtained by regional impedance tomography can be used to determine an optimal therapeutic level of the so-called positive end-expiratory pressure (PEEP). It is important to find an optimal biological compromise between treating alveolar overdistension in one part of the lung and atelectasis in another. As a priority, PEEP levels must be set high enough to prevent as much as possible the collapse of alveoli at the end of expiration in the most dependent parts of the lung; at the same time the over-stretching of the non-dependent upper parts on the lungs must be avoided. Both these pathological conditions—alveolar collapse and alveolar overdistension—can be recognized as a reduced amplitude of the ventilation-induced impedance changes in a regions of interest. An optimal level of PEEP, however, leads to an even distribution of ventilation (and thus impedance changes) throughout the entire lung.

In addition, an optimal level of PEEP prevents the collapse of airways. If airways are kept open during the entire respiratory cycle, the respiratory gases are exchanged efficiently. These parts are thus ventilated and the impedance signals follow this ventilation. If, however, the conducting airways are collapsed during the entire respiratory cycle, the terminal lung units—in particular the alveoli—are cut off from the supply of fresh gas. Gas exchange suffers and no ventilation-induced change in the impedance signal can be detected. These lung areas become silent on the impedance tomographic image. The oxygen within the cut-off alveoli is absorbed and with the progressive decrease in their gas content, the absolute impedance of such a lung unit is reduced. In a scenario where PEEP levels are not high enough to prevent the expiratory collapse of airways and terminal lung units (alveoli) but where pressures are sufficiently high to open collapsed airways during inspiration, ventilation of these lung units takes place only during this period of the respiratory cycle. The changes in the impedance signals of such a lung region can be amplified compared to an area of normal ventilation since these collapsed lung units start from a low expiratory air content but are filled rapidly to approximately normal volumes during inspiration. During expiration they collapse, again and the process of tidal recruitment/collapse begins anew.

Observing the signals from regional impedance tomography it is possible to determine the points of airway/alveolar opening and closing by systematically titration inspiratory and expiratory airway pressures.

In accordance with a further aspect of the present invention, the apparatus comprises a monitoring unit for monitoring the first respiration pressure value and the second respiration pressure value. By monitoring these values the patient can be observed by a monitoring device gaining important pieces of information with regard to the lung functioning. All the direct and derived impedance signals and/or images discussed above should be calculated continuously and should be available for on-line display. Any single one of them or a combination of them can be used for the automatic or semi-automatic control of a therapeutic device, such as a mechanical ventilator. The information obtained by electrical impedance tomography can be used to guide specific clinical maneuvers aiming at optimal lung recruitment and at keeping most alveoli open or at finding the best biological compromise between alveolar overdistension and alveolar collapse.

Furthermore, regional pressure-volume curves generated by electrical impedance tomography can be used to define pressure points of specific clinical relevance. These points are the alveolar opening and closing pressure of a specific lung region, the lower and the upper inflection point of the inspiratory and the expiratory pressure-volume curve. Additional information on lung behavior can be obtained by analyzing the shape and the area the pressure-volume-curve.

Further details and advantages of the invention will be explained in more detail on the basis of the example of an embodiment shown in the drawing. It shows:

BREIF DESCRIPTION OF THE FIGURES

Figure 2B:
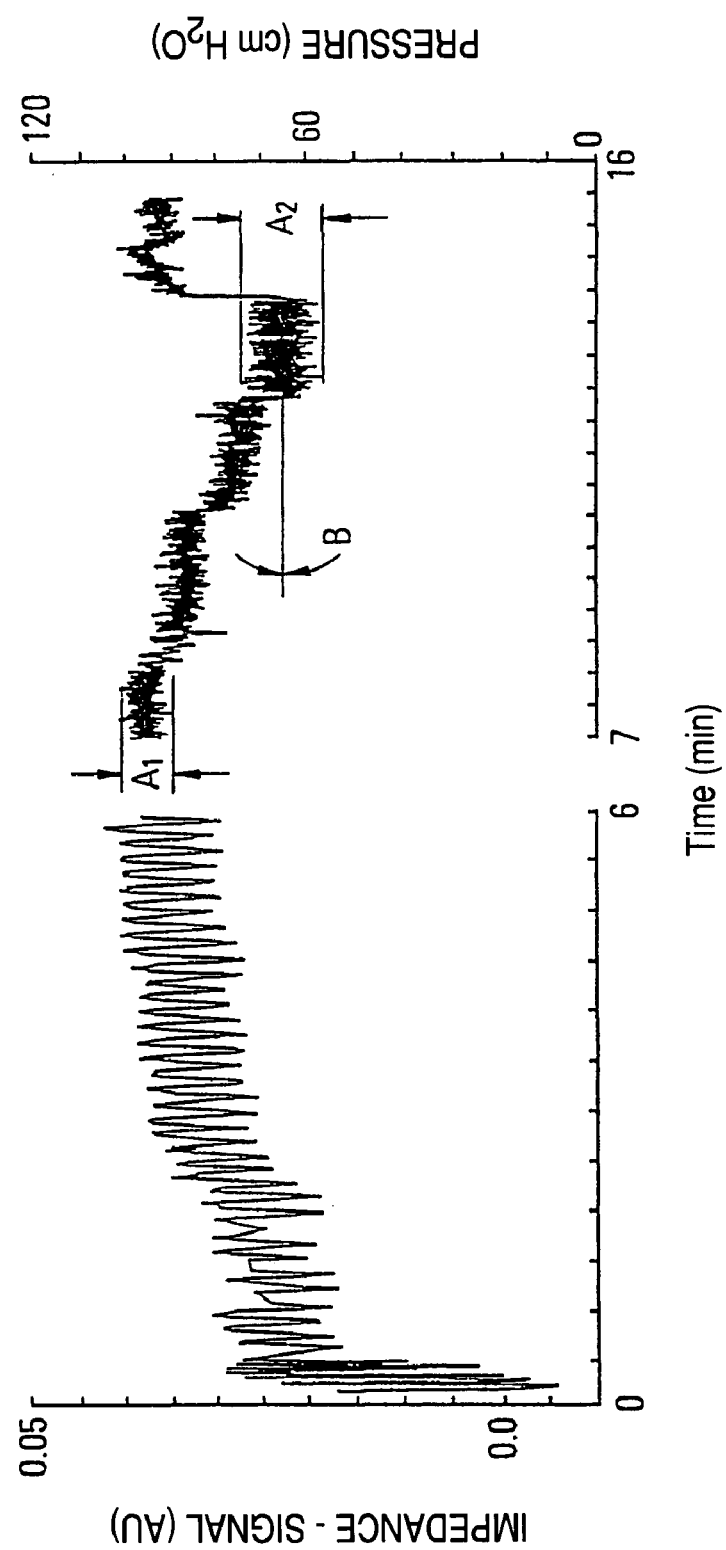
Figure 2C:
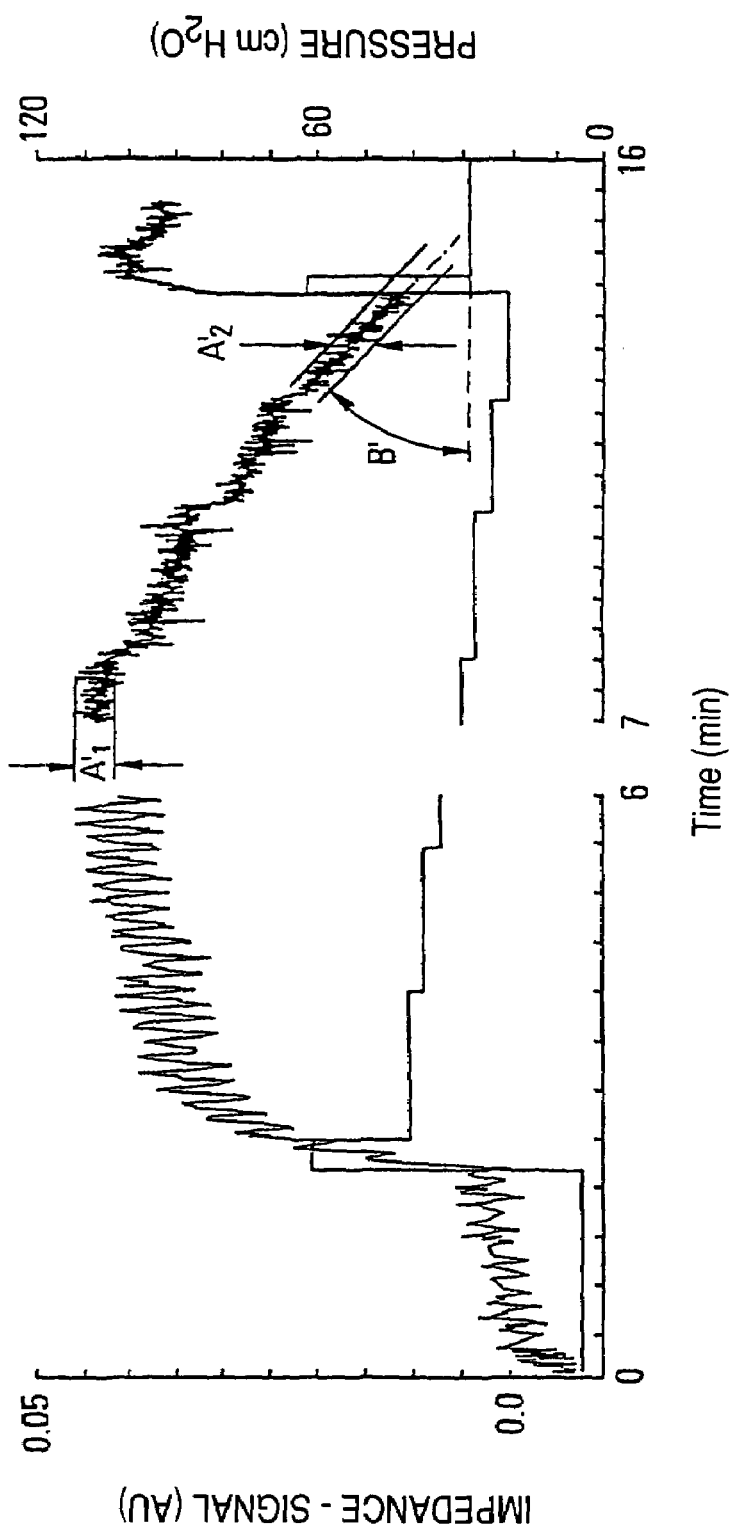
Figure 3A:
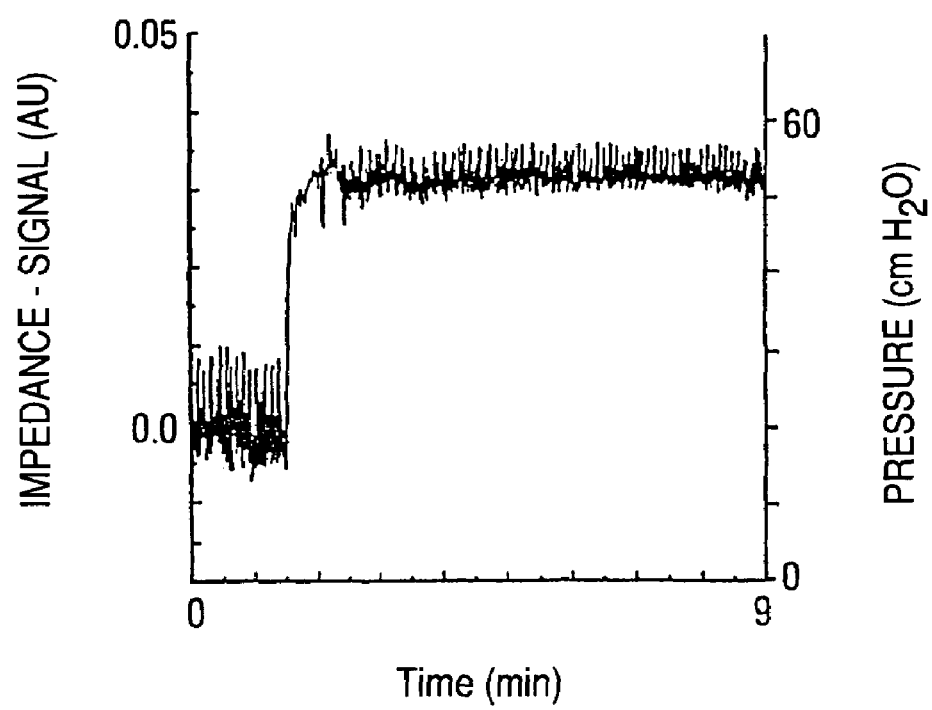
Figure 3B:
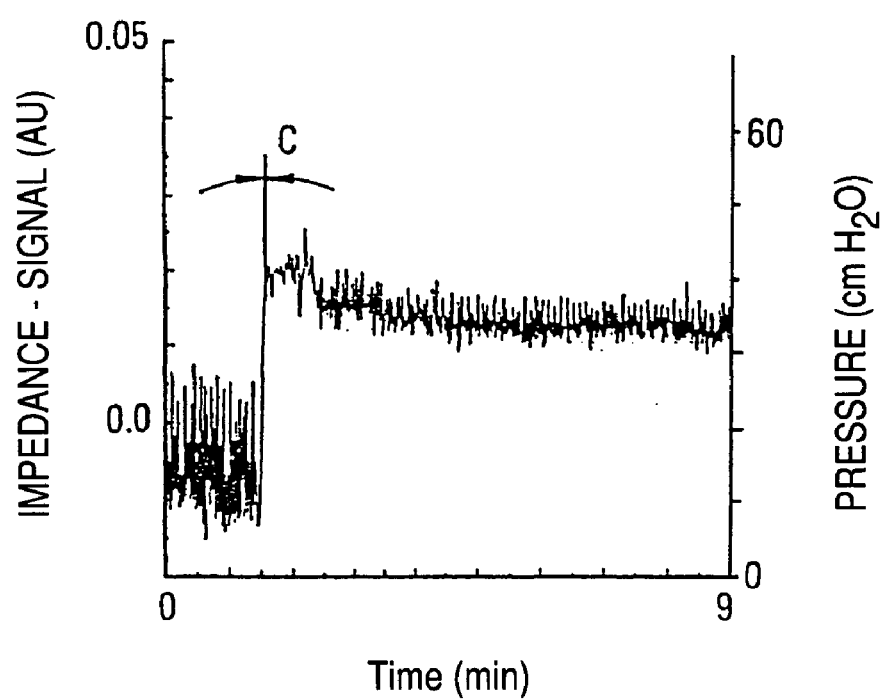
Figure 3C:
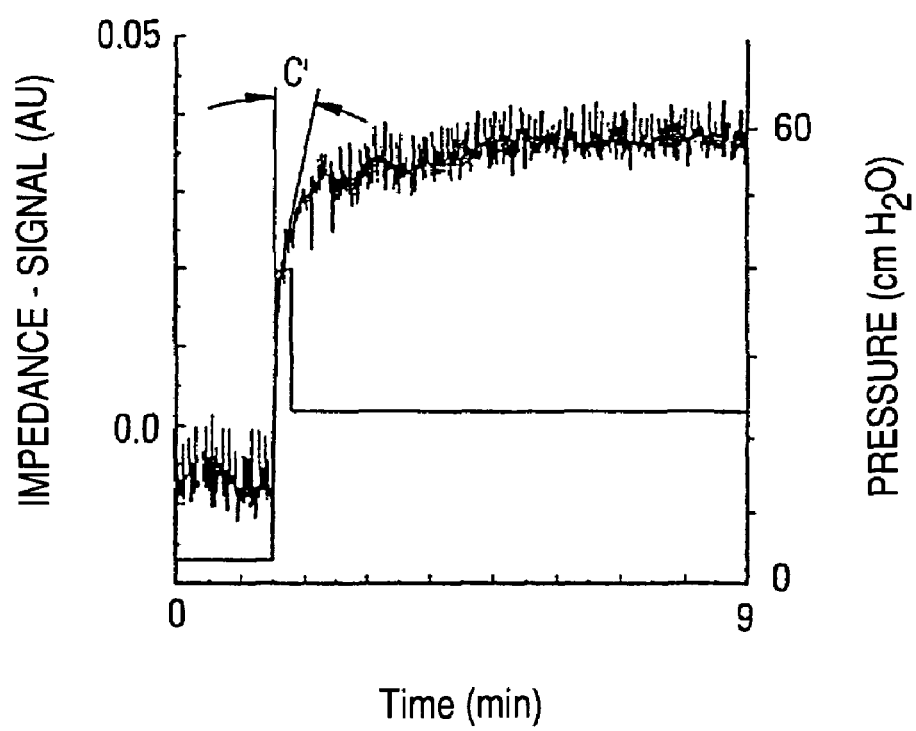
Figure 4:
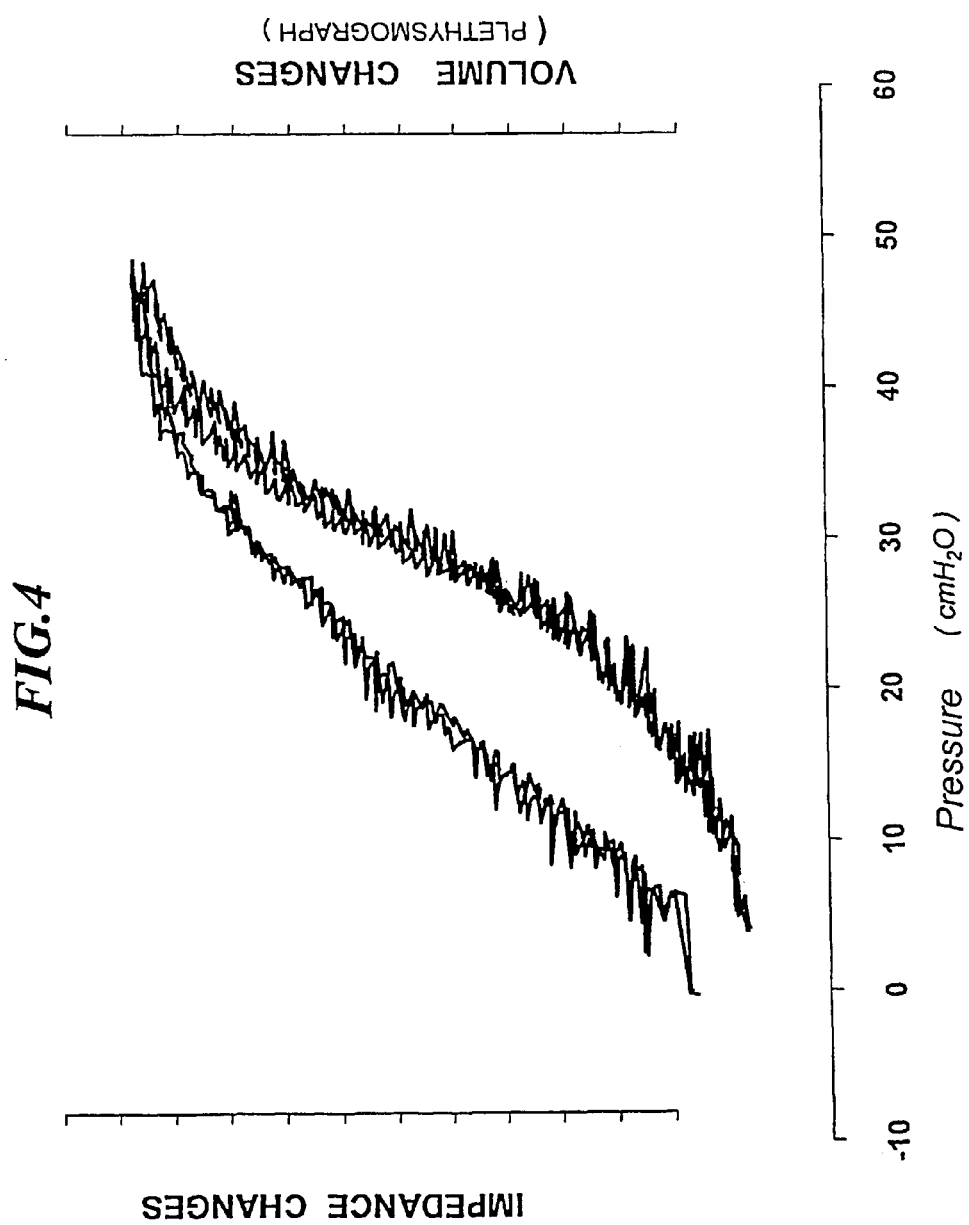
Figure 5:
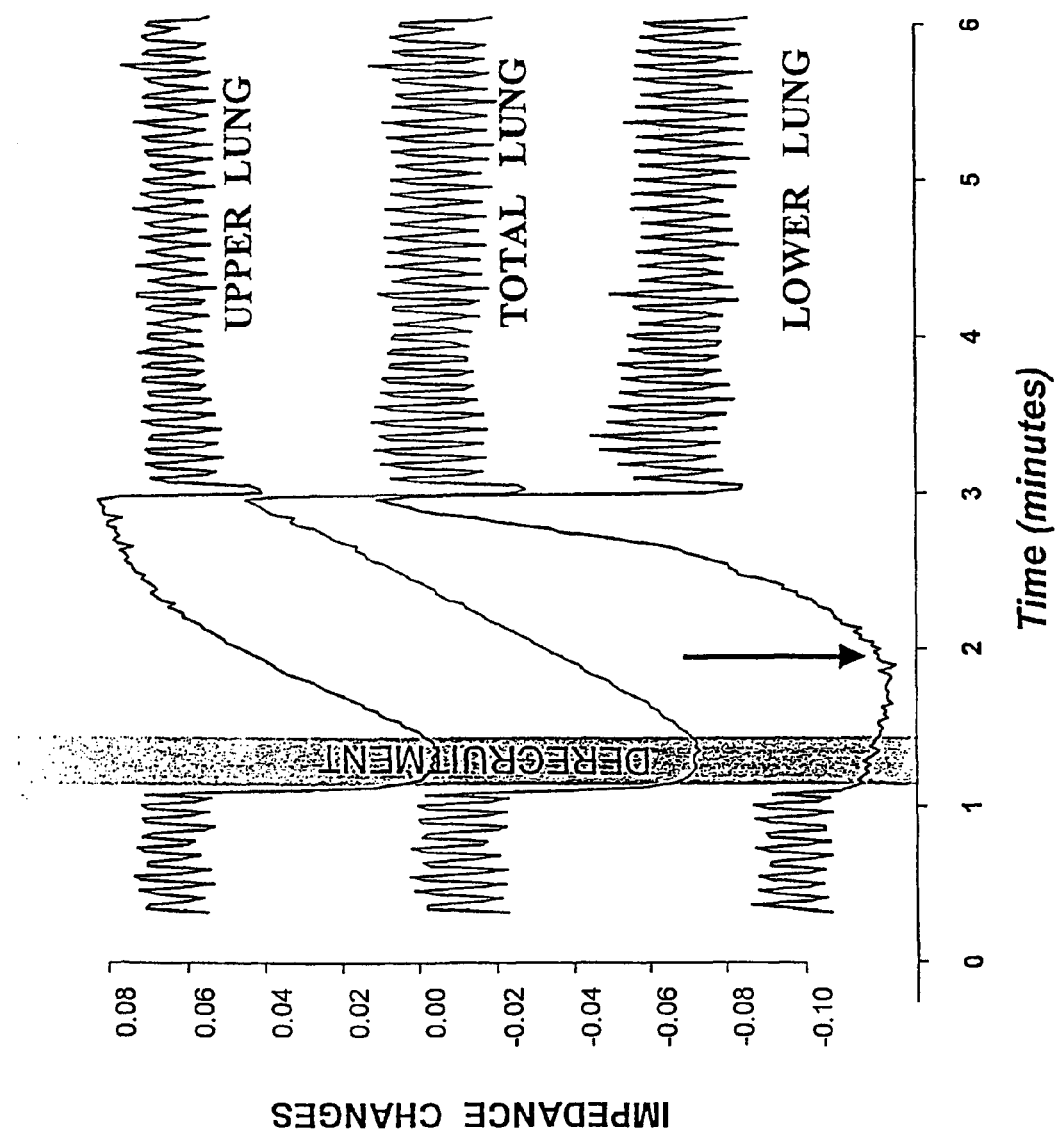
Figure 6:
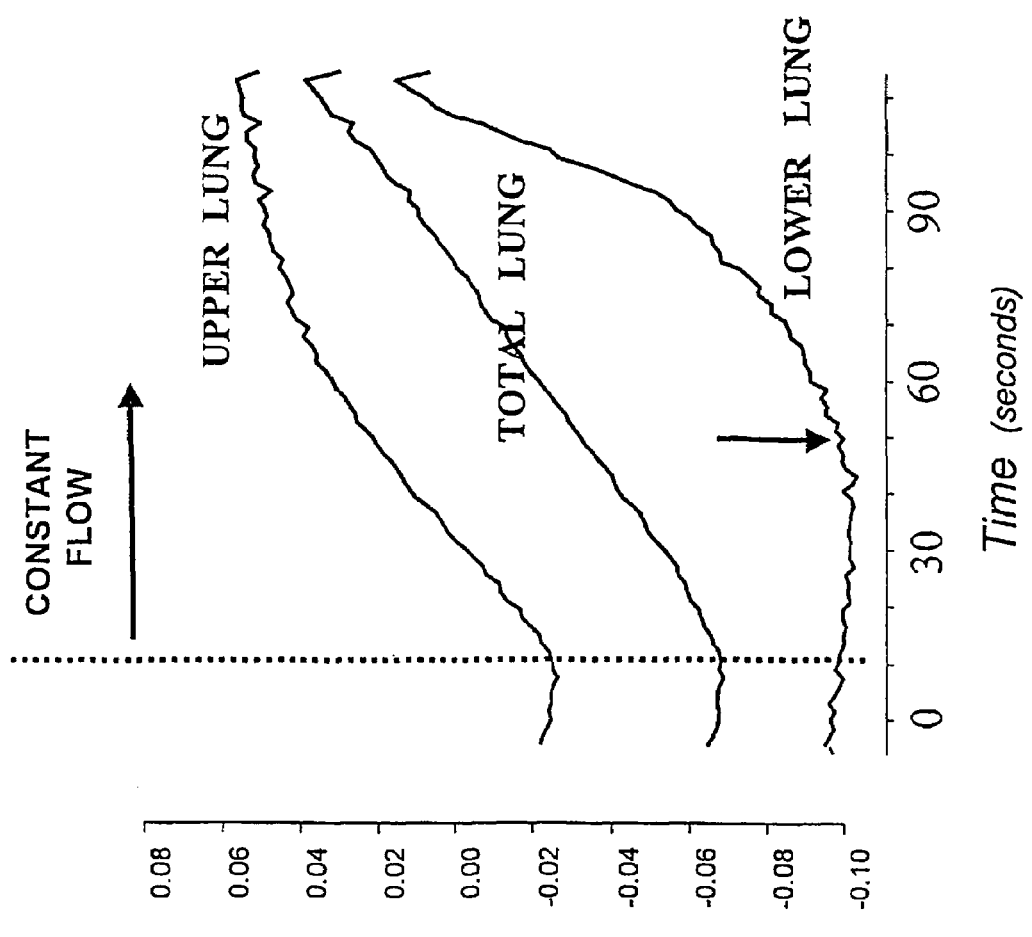
Figure 7:
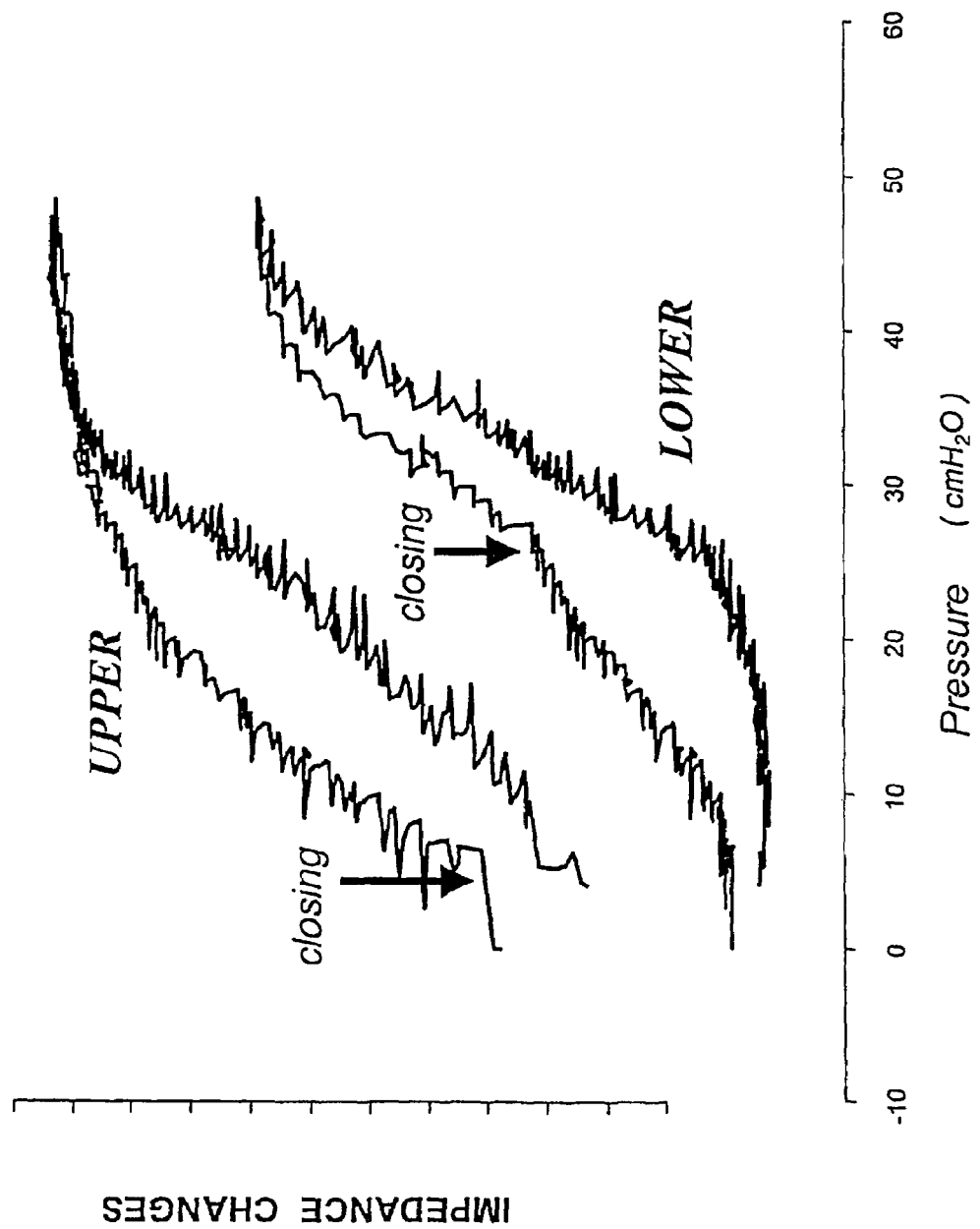
Figure 8:
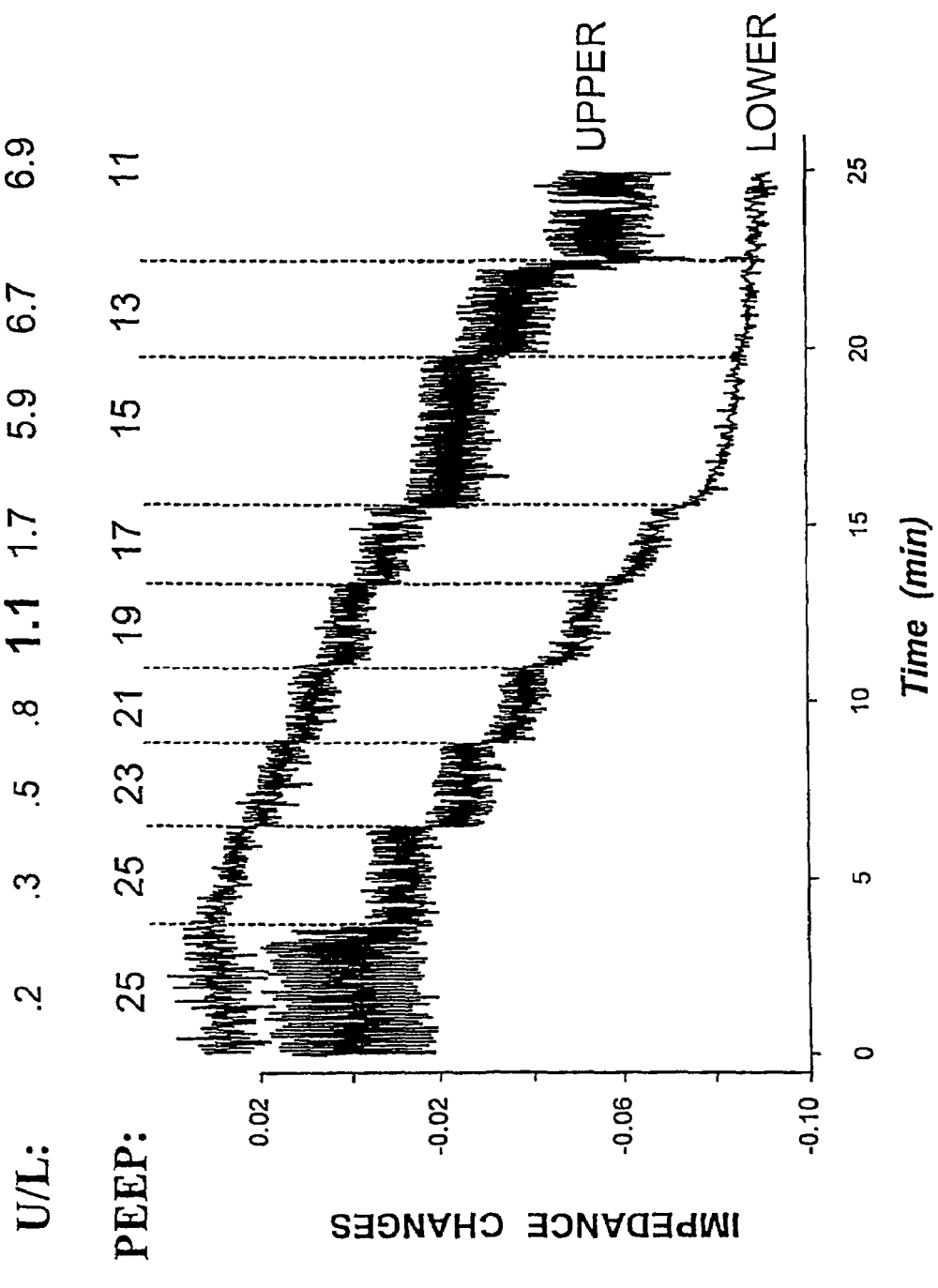
Figure 9:
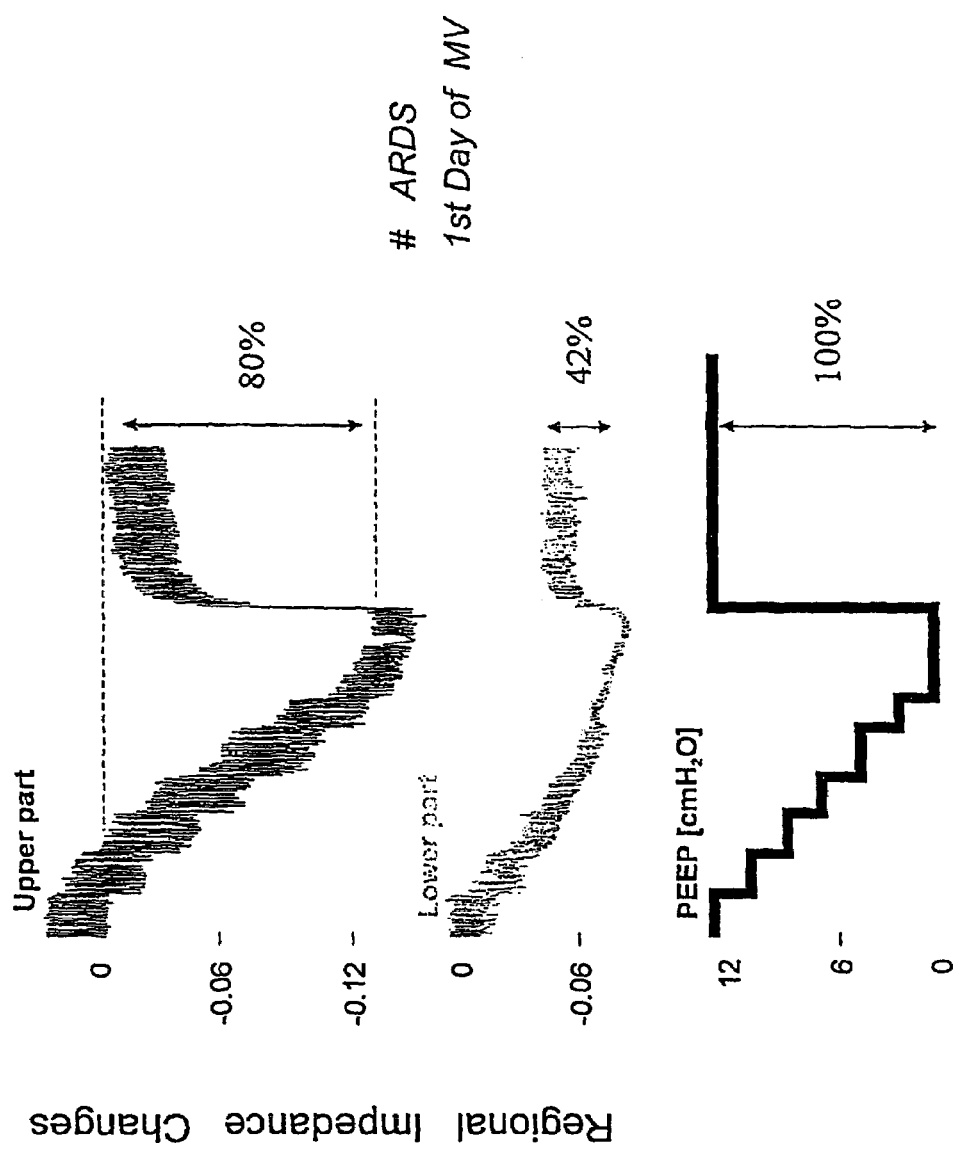
Figure 10:
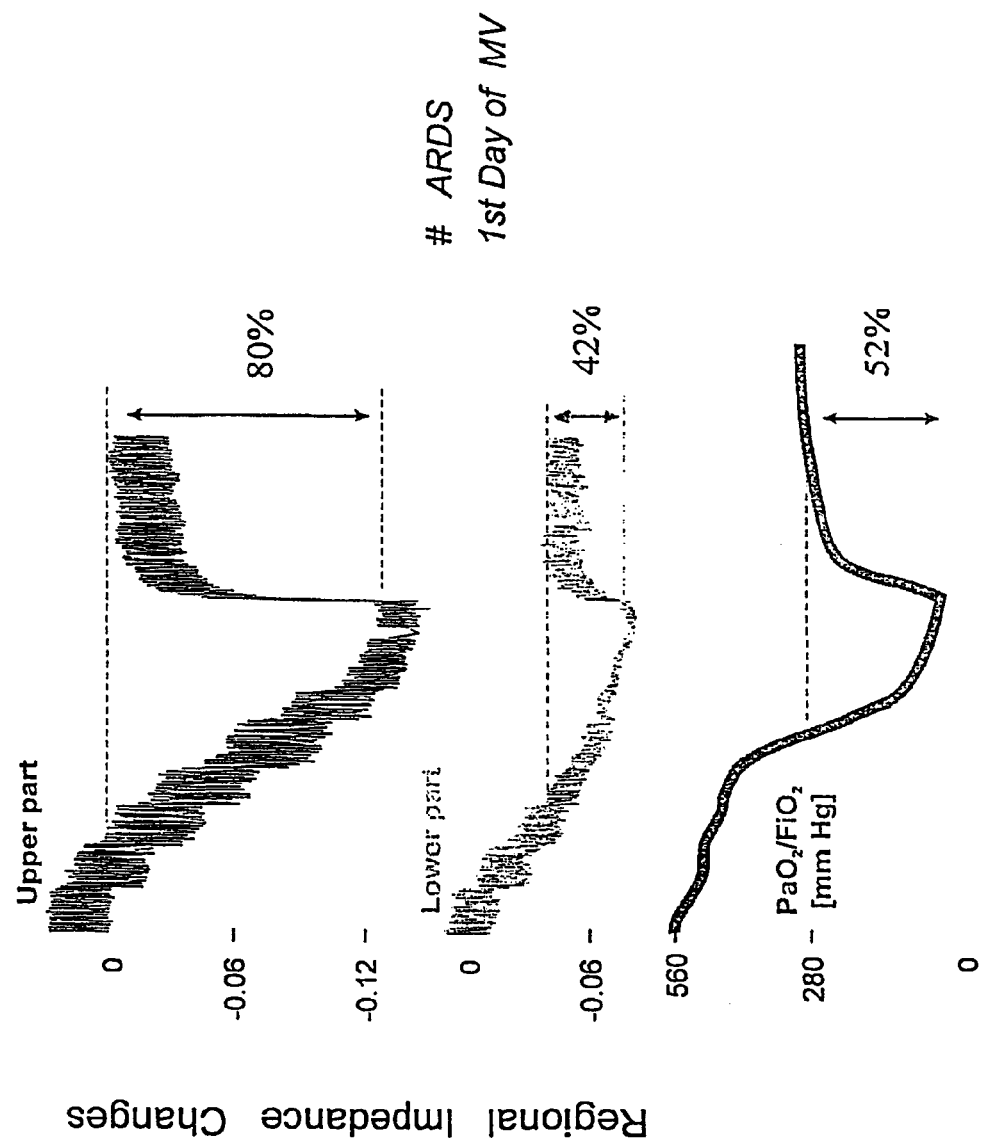
Figure 11:
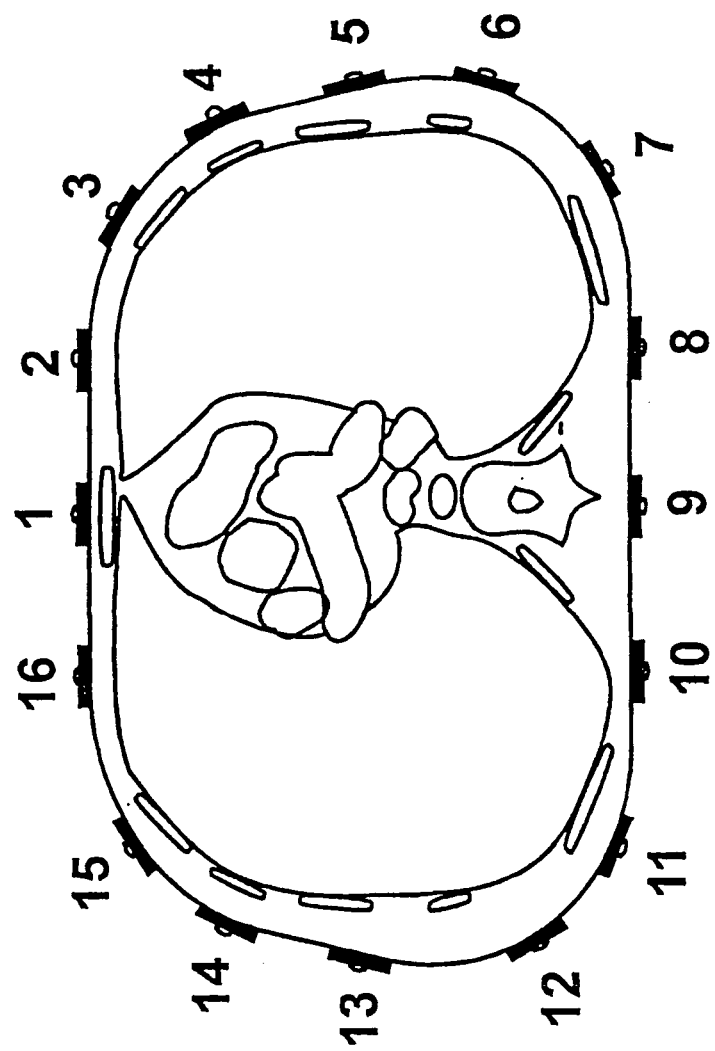
Figure 12:
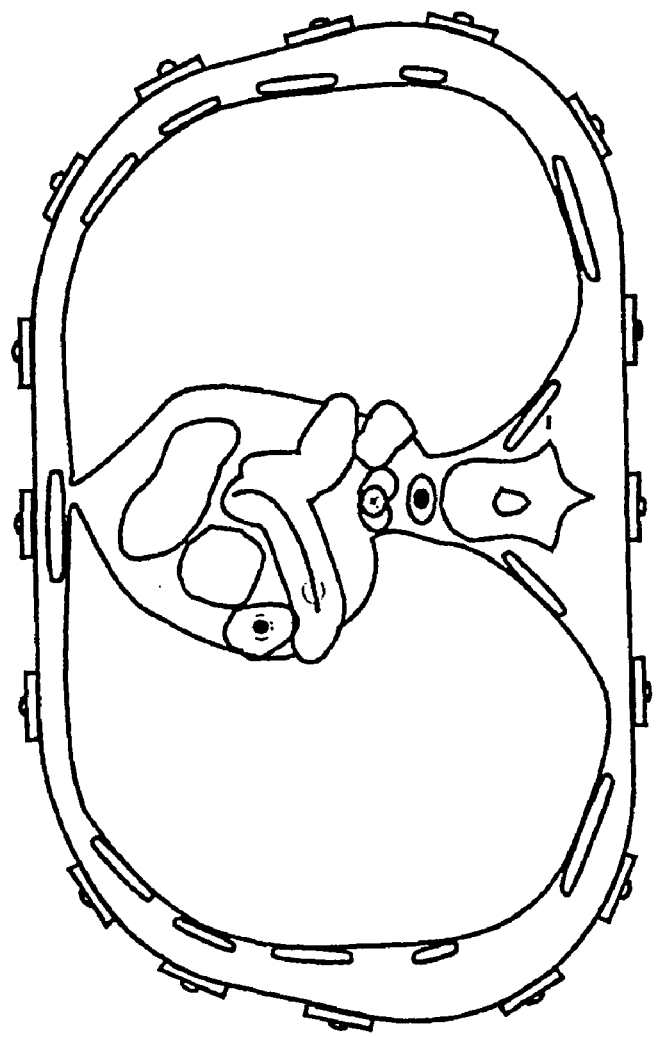
Figure 13:
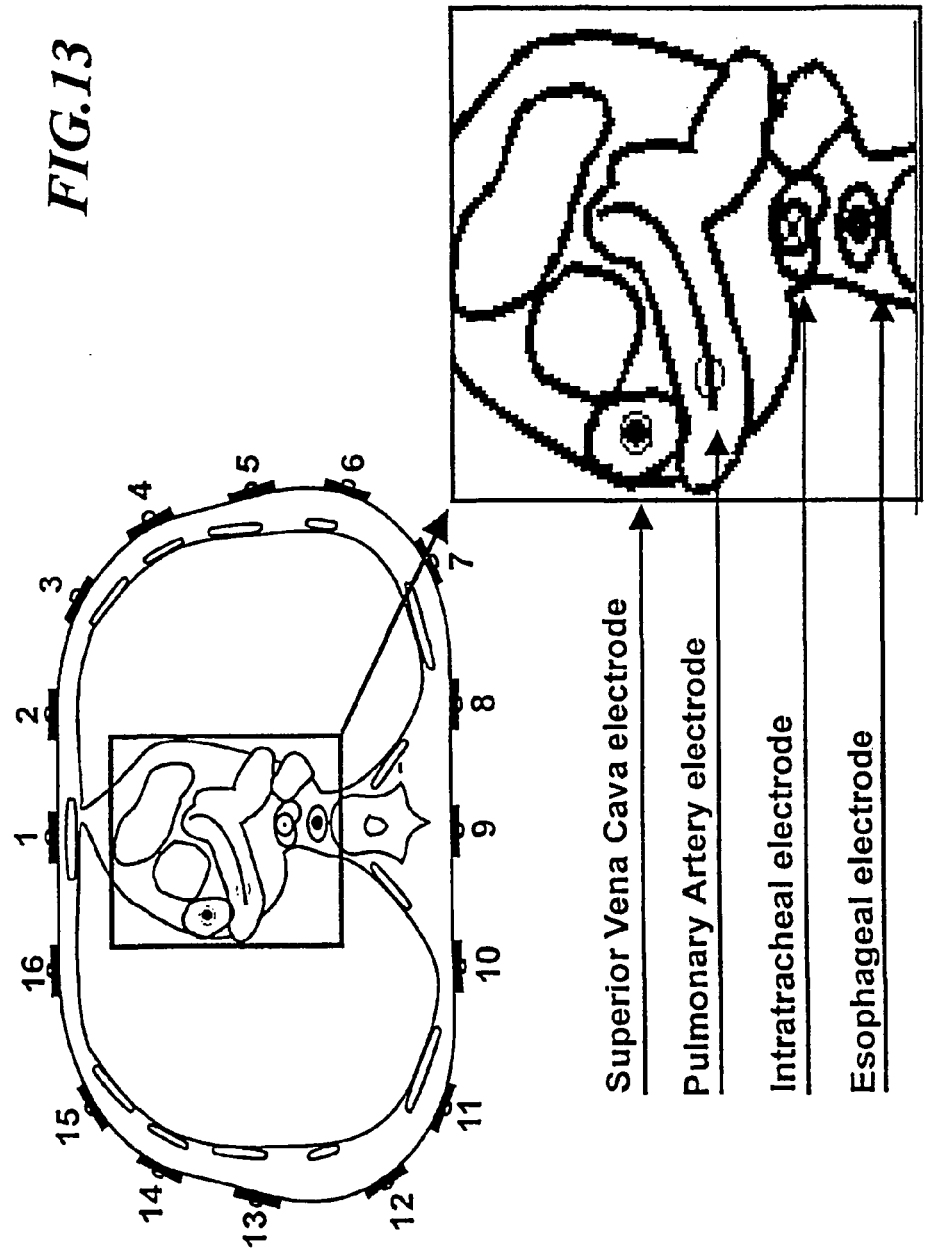
Figure 14:
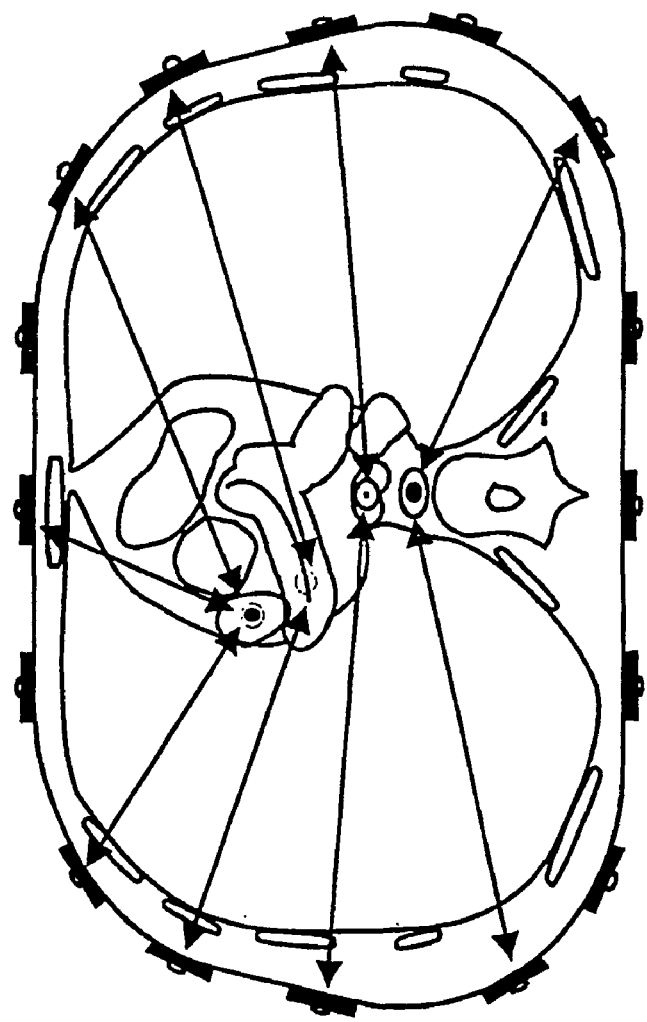
Figure 15:
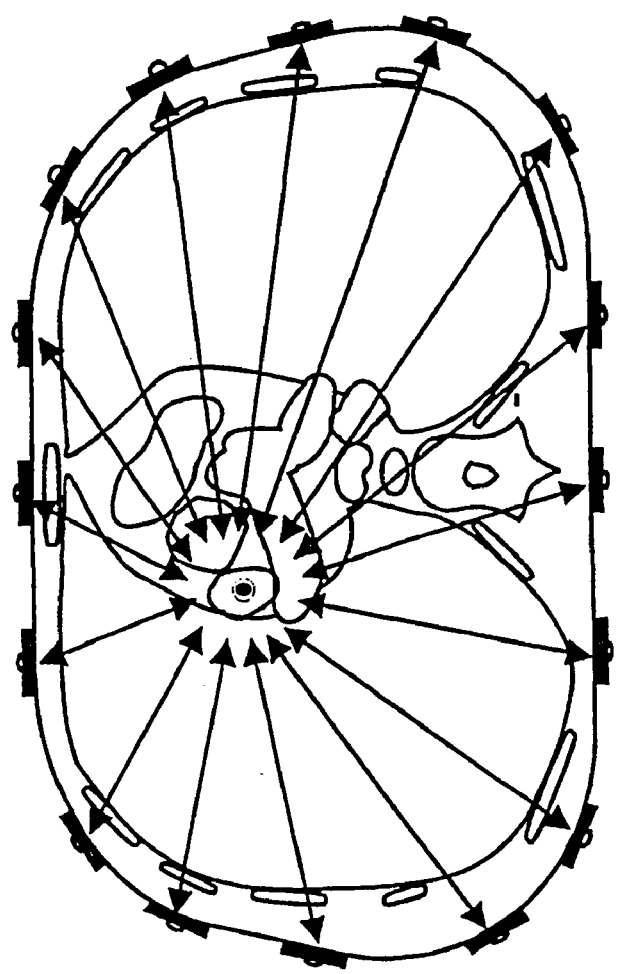
Figure 16:
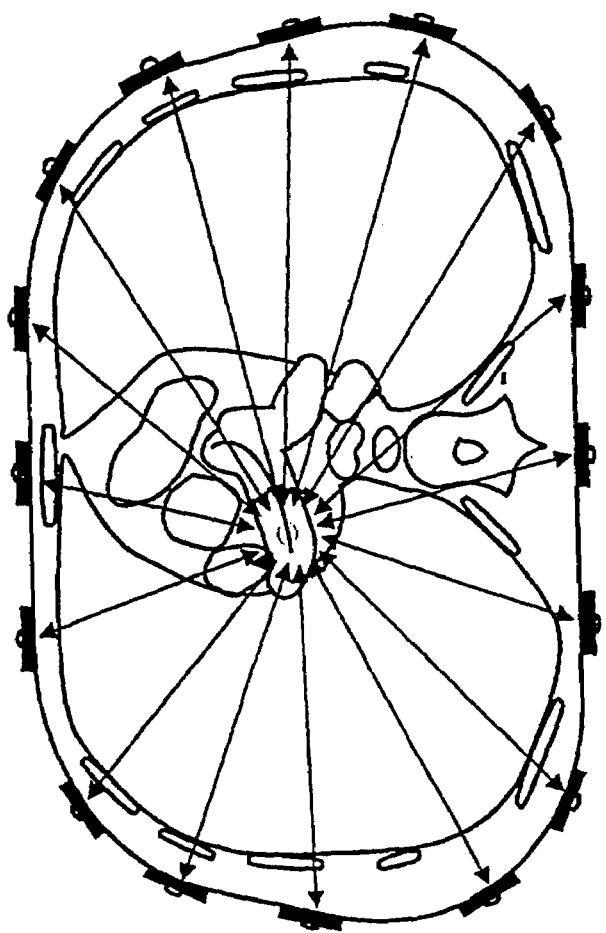
Figure 17:
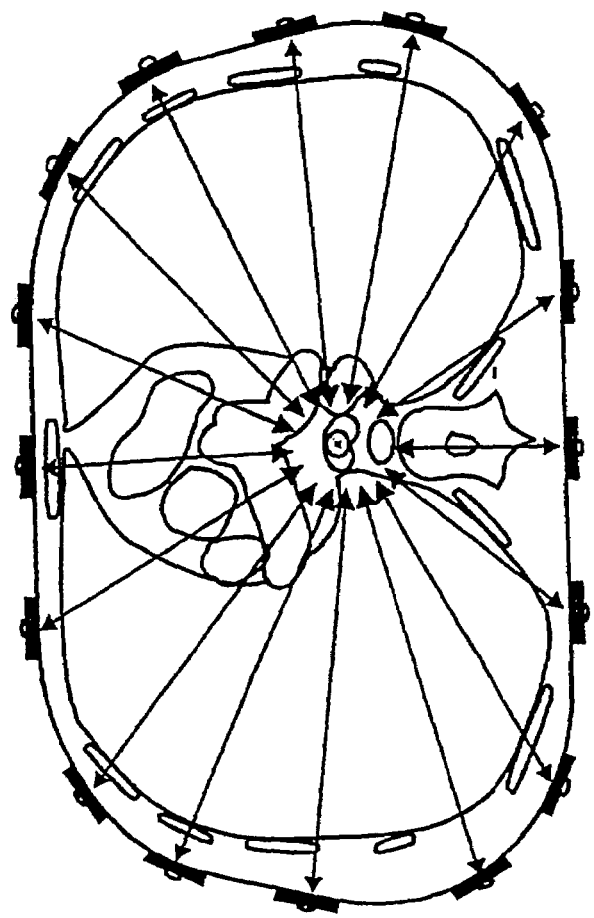
Figure 18:
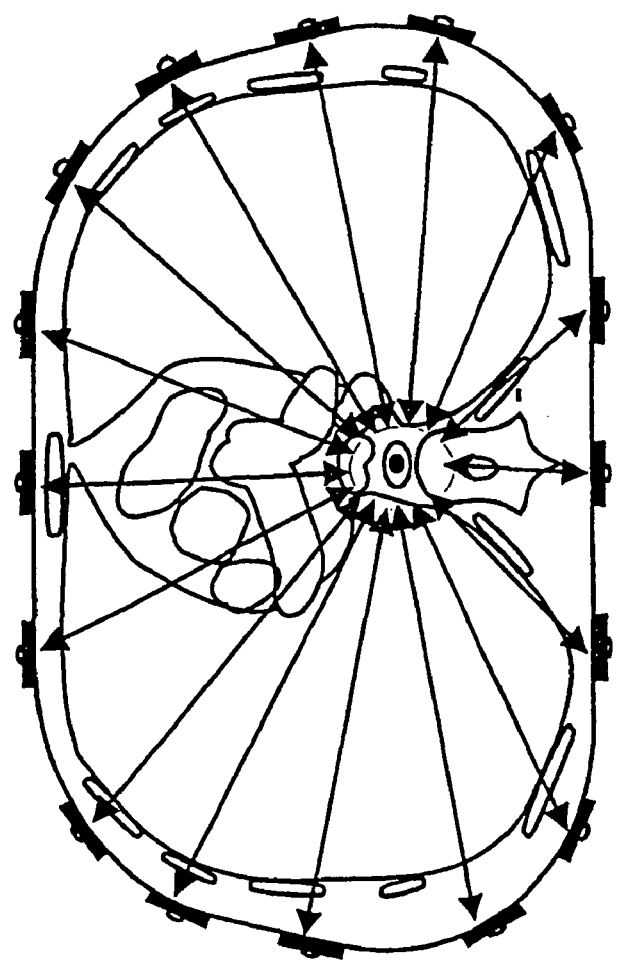

FIG. 1 pressure-impedance curves in four different zones of the lung,

FIG. 2a an impedance signal depending on time for the entire lung,

FIG. 2b an impedance signal depending on time for the upper zone of the lung,

FIG. 2c an impedance signal depending on time for the lower lung zone with the relevant pressure curve for FIGS. 2a, 2b and 2c, FIG. 3a an impedance signal depending on time for the entire lung zone, FIG. 3b an impedance signal depending on time for the upper lung zone, and FIG. 3c an impedance signal depending on time for the lower lung zone with the relevant pressure signal for FIGS. 3a, 3b and 3c, FIG. 4 a superimposition of a pressure-impedance and a pressure-volume curve of an entire lung during inflation and deflation, FIG. 5 three curves indicating the changes of impedance during mechanical ventilation as a function of time, FIG. 6 impedance signals of the upper and the lower parts of the lung together with the signal of the total lung during a slow insuflation at a constant flow of oxygen, FIG. 7 independent inflation-deflation pressure-impedance curves of the upper and the lower part of the lung, FIG. 8 impedance curves of the upper and lower parts of the lung at decreasing levels of positive end-expiratory pressures (PEEP), FIG. 9 impedance curves of the upper and the lower lung of a patient suffering from severe lung failure, and FIG. 10 impedance curves according to FIG. 9 together with an arterial oxygenation index, FIG. 11 an external electrodes set up, FIG. 12 an internal electrodes set up, FIG. 13 an electrical impedance tomography internal and external electrodes set up, FIG. 14 shows a electrical impedance tomography set up with internal electrodes using an intratracheal catheter, an esophageal catheter, a pulmonary artery catheter and a superior vena cava catheter, FIG. 15 shows a superior vena cavae internal electrode set up, FIG. 16 shows a pulmonary artery (swan-ganz) internal electrode set up, FIG. 17 shows an intra-tracheal tube internal electrode set up and FIG. 18 shows an esophageal tube internal electrode set up.

DETAILED DESCRIPTION OF THE INVENTION

FIG. 1 shows pressure-impedance curves according to electrical impedance tomography in four different zones of the lung. In comparison with the known pressure-volume curves, the corresponding pressure-impedance curves show a similar course. As from a certain pressure point, the first alveoli (terminal lung units or air sacks) change over from the state of collapse to the state of opening. When the pressure is further increased, more and more closed alveoli are opened until the opening finally ebbs away and at higher pressures forms the flat part of the impedance signal. Comparison of the individual curves over the various zones of the lung shows that the opening phenomenon is not homogeneously distributed over the entire lung in this case. The measurements are carried out according to the method of electrical impedance tomography, wherein the zones 1 to 4 in the direction of the gravity vector subdivide the lung into planes which are perpendicular thereto. In the uppermost zone of the lung, the expected pressure-impedance distribution appears, whereas in the regions 2 to 4, increasingly pathological manifestations of the closing phenomenon are seen to be recognized. For example, pathological changes in the lung may be caused by oedema formation (increased accumulation of liquid in the case of inflammation), whereby the lung is heavier in the direction of the gravity vector. Inter alia, above all the lowest parts of the lung are compressed thereby and therefore can only open at a later point in time or at higher pressures.

FIGS. 2a, 2b and 2c show impedance signals depending on time for different zones of the lung, wherein as the pressure signal, the pressure signal marked in FIG. 2c respectively forms the basis. After one half of the paths of the curve, there is respectively a change in the scale, wherein in the second half of the figures, the path of the curve is correspondingly compressed. FIG. 2a shows an impedance curve for the total zone of the lung, whereas the path of the curve according to FIG. 2b concerns the upper zone and the path of the curve according to FIG. 2c refers to the lower zone of the lung. In FIG. 2c the underlying pressure signal is marked, which refers to all three figures. Accordingly the respiration pressure is suddenly increased after a certain initial time and then it is reduced step by step, until another pulse follows. The lower zone of the lung is in its turn pathologically altered. According to the invention, this pathological alteration can be discerned in the curves which are shown, in particular, on the basis of two processes:

On the one hand it is possible to evaluate the change in the impedance signal due to breathing movements. They are expressed in the impedance signal in high frequency oscillations, the sinusoid course of which is to be discerned in the first half of the signals. When one compares the changes in the impedance signal on the basis of breathing movements according to the parameters A1 and A1' it is noticeable that the breathing movements in the upper zone of the lung cause larger impedance changes than in the lower zone of the lung. In addition it is striking that this phenomenon is dependent on respiration pressure, as a comparison of the magnitudes A2 and A2' shows.

Another process according to the invention for the regional determination of alveolar opening and closing of the lung consists of the evaluation of the mean change in the impedance signal based on the collapse of the alveoli. This effect is marked in FIGS. 2b and 2c by the magnitudes B and/or B'. The impedance signal according to FIG. 2b fluctuates at constant pressure around a constant offset, whereas in the impedance signal according to FIG. 2c, a drop in the impedance signal is also to be seen at constant pressure. Consequently the ascending gradient B and/or B' makes a statement as to whether collapse of the lung is taking place.

FIGS. 3a, 3b and 3c show an impedance signal as the response to a pulse-shaped pressure increase, which is shown in FIG. 3c. In the lower zone of the lung according to FIG. 3c, the pulse signal responds thereto with a delayed response, whereas the impedance signal according to FIG. 3b follows the pressure increase without delay. Therefore a method for regional determination of the alveolar opening and closing of the lung can be derived from the change in the impedance signal on the basis of respiration pressure changes. For example, this change can be inferred from the initial gradient of the impedance signal on pressure changes.

Another possibility is to analyse the phase difference during conventional tidal breaths between different lung zones. Having two wave forms of tidal breaths of the impedance signal, one from the upper level and one from the bottom level, the change in the impedance signal on the basis of respiration pressure changes can be calculated from the phase difference between these two sinusoidal-like curves. This kind of analysis showed also very consistent results.

In summary, there are at least three possibilities to determine the alveolar opening and the alveolar closing of the lung from the impedance signal: Firstly, regional amplitudes detected as the distance between peaks and valleys during tidal breaths or just as the standard deviation of the signal during a certain period of time can be analysed, either for one region or as a comparative method for different regions. Secondly, knowledge-based methods can be introduced as shown e.g. according to FIG. 2c where the impedance curve shows a behavior which differs from the expected behavior of a healthy lung. Furthermore, it can be use of temporal delays of inflation of the impedance signal, either in one region or among different regions.

FIGS. 4 to 10 show additional impedance curves of a patient with a sick lung. As described above, the lung is made heavier by the oedema formation, i.e. because of increased accumulation of liquid in the case of inflammations. Thereby a gravity depend gradient results from the sternum to the spinal column. Thereby above all the lowest parts of the lung are compressed and collapse.

FIG. 4 shows a superimposition of a pressure-impedance and a pressure-volume curve of an entire lung during inflation and deflation.

FIG. 5 shows three curves indicating the changes of impedance during mechanical ventilation as a function of time. The uppermost curve represents the upper, the lowest curve the lower part of the lung. The middle curve represents the impedance changes of the entire lung (upper and lower parts together). After an initial phase of steady state, ventilation is stopped. The lungs collapse immediately (they de-recruit). Then, the lungs are inflated with a constant flow of breathing gas. Note the delay in time (indicated by the arrow) before the impedance of the lower part of the lung begins to show a positive change in its impedance signal. Thus, a considerable time lag in the recruitment of alveoli in the lower, most dependent part of the lung is noticed. After the successful recruitment manoeuvre, a new steady state of ventilation is reached. Now, the amplitude of the signal and the mean level of impedance in the lower part have both increased.

FIG. 6 shows impedance signals of the upper and the lower parts of the lung together with the signal of the total lung during a slow insufflation at a constant flow of oxygen. The upward convexity of the upper curve indicates a distension of open alveoli as lung volume increases. The upward concavity of the curve representing the lower lung areas indicates a delayed (arrow) opening of collapsed lung units. The steep slope of the curve beyond 90 seconds shows that the recruitment process is still going on without ever reaching a saturation as in the upper lung. As can be expected from the experimental set up the curve of the total lung is almost a straight line; it represents the change in the air content of the total lung. It increased linearly with time.

FIG. 7 shows independent inflation-deflation pressure-impedance curves of the upper and the lower part of the lung. Compared to the upper curve the lower curve is shifted towards the right, indicating a delayed opening of dependent alveoli. As opposed to the upper lung, the lower one does not show a saturation behavior of its impedance changes at high away pressures. Thus, in the dependent lung zones the recruitment of collapsed alveoli still incomplete even at airway pressures as high as 50 cmH2O. On the deflation limb, when airway pressures are reduced, collapse of the lower lung regions occurs earlier than in the respective upper lung zones (arrows indicate alveolar closing).

FIG. 8 shows impedance curves of the upper and lower parts of the lung at decreasing levels of positive end-expiratory pressures (PEEP). The impedance amplitude of the upper lung (U) is divided by the amplitude of the lower (L) lung. The U/L-ratio is given in the top line. With decreases in PEEP the mean impedance of these lung units decreases, too. At high PEEP levels the upper lung zones are distended (small amplitude) and ventilation is shifted to the lower lung zones (large amplitude). The U/L ratio remains below 1. Once overdistension is relieved, ventilation is distributed more evenly (U/R 1). Once PEEP becomes too low to keep all lung units open, alveoli start to collapse. The amplitude of the impedance signal of the lower lung decreases and shifts to the upper lung regions. The U/L ratio exceeds 1. Finally, hardly any ventilation-induced impedance change can be seen in the lower curve.

FIG. 9 shows impedance curves of the upper and the lower lung of a patient suffering from severe lung failure (adult respiratory distress syndrome, ARDS) on day one on mechanical ventilation. PEEP is stepwise decreased from 12 to 0 cmH2O. Initially, as distension is overcome, the amplitude of the impedance in the upper lung zones increases at the expense of the ventilation of the respective lower lung zones. Finally, at a PEEP level below 4 cmH2O a decrease in the impedance amplitude indicates that alveolar collapse has also occurred in the upper lung zones. When, after this collapse, the PEEP level is returned to its original level (100%), the lung zones do not reach their original state of inflation, again. Despite the same distending pressure, the upper part achieves 80%, the lower lung only 42% of its original impedance (thus volume).

FIG. 10 shows two curves which are the same as before. In addition, arterial oxygenation index (PaO2/FiO2) is shown in the lower line. The open lung is characterized by a PaO2/FiO2>500 mmHg. As PEEP is decreased, the lower lung units start to collapse and ventilation is shifted towards the upper lung zones. This way, the loss of gas exchanging alveoli in the lower part of the lung is at least partially compensated. Oxygenation index decreased only slowly. Once, however, the PEEP is no longer high enough to stabilize the upper lung zones, their collapse is indicated by a steep drop in oxygenation curve. Even when setting the PEEP back to the original value, the loss of functional lung units is not reversed. Only 52% of the baseline oxygenation can be achieved.

As already mentioned above, the invention can make use of an electrical impedance tomography apparatus. However, it has to be observed that several adoptions and variations of the conventional electrical impedance tomography apparatus are possible to optimise the measurement according to the invention. This optimisations are described in the following with reference to the FIGS. 11 to 18.

FIG. 11 shows an optimised external electrodes set up according to the invention. In order to overcome the known contact problems of conventional skin electrodes (high resistance to electrical currents, poor contact between skin and electrode, displacement and electrical noise with motion and breathing, etc) electrical bobbins to generate and detect magnetic field could be used. These could be arranged on circular band around the thorax or on catheters within the body. Alternatively the bobbins could be mounted on a fixed frame that encompasses the thorax. This frame could then be moved relative to the longitudinal direction of the body to obtain tomographic or spiral images of different segments of the thorax.

Furthermore, it should be noted that the number of electrodes can be increased from 16 to 32 or more electrodes in order to improve the resolution of the signal obtained by regional electrical impedance tomography even more.

FIG. 12 shows an internal electrodes set up according to the invention. Generally speaking, the set up according to FIG. 12 is based on the cognition that the distance between the electrodes should be reduced. It is conceivable that electrodes or bobbins could be mounted on tubes and catheters that are placed within the body. Since both the trachea and the esophagus are located in the approximate centre of the thorax endotracheal and/or naso-gastric tubes could be used as electrical centres for the generation of regional electrical impedance tomographic images. Furthermore, catheters brought into the blood stream, such as central venous or pulmonary artery catheters could serve a similar purpose. Bobbins or electrodes could be placed on one single or on multiple locations along the tubes and/or catheters in order to obtain images at different locations within the chest. It could be feasible to use one or more of these tubes and/or catheters at the same time. Depending on the clinical situation of the patient, tomographic images of the electrical impedance of the chest can thus be generated by using external electrodes/bobbins around the thorax alone or by combining them with internal electrodes/bobbins as described above. Any one of the catheters or tubes has to be designed according to the needs defined by its general clinical purpose and by its specific function within the impedance tomography setting.

FIGS. 13 and 14 show a set up in which all electrodes of the internal set up according to FIG. 12 are used for electrical impedance tomography measurements. As it becomes from FIG. 14, the distances between the electrodes can be reduced significantly.

Images and signals from regional electrical impedance tomography can be used to detect clinically important and dangerous situations instantaneously. If the endotracheal tube is placed in the correct anatomical position within the trachea, both lungs are ventilated evenly. If, however, the tube is advanced too far only one of the two main bronchi is intubated; thus only this one lung is ventilated. The EIT-signal for the non-ventilated lung will be electrically silent whereas the other half of the lung shows a normal or an increased intensity.

To detect this condition, the regional impedance signal of a representative part of each lung has to be determined. If the ventilation-induced impedance change falls below an expected reference value a high suspicion for the presence of an incorrect intubation is generated. In the presence of such a suspicion the magnitude of the local impedance change of the right has to be compared with that of the left lung. If the difference exceeds a certain threshold, a one-sided intubation can be diagnosed with certainty.

If—for whatever reason—lung tissue is disrupted and free air gets into the space between the lung and the rib cage (pneumothorax) or in a spaces within the lung (bulla), this pathological accumulation of air will, after an initial increase in local impedance, show a markedly reduced or no further change in its impedance. This region will become "silent" on the EIT-image. The cyclic ventilation of the surrounding lung tissue demarcates the pneumothorax or bulla. A similar but opposite change in the impedance properties (a reduction) can be seen if fluid accumulated in the space between the lung and the rib cage (pleural effusion). Again the ventilated lung tissue demarcates the pathological fluid accumulation.

FIG. 15 shows a set up where only the superior vena cavae is used for an internal electrode set up. Accordingly, FIG. 16 shows a pulmonary artery (swan-ganz) internal electrode set up. Furthermore, according to FIG. 17, the intra-tracheal tube is used for an internal electrode set up. Eventually, according to FIG. 18, the esophageal is used for an internal electrode set up. Intrapulmonary, intra-abdominal and esophageal pressures can be measured by the appropriate tubes or catheters (i.e. endotracheal, esophageal or gastric tubes, urine or intra-abdominal catheters). Each one of these pressures, a combination of them or a difference between them can be plotted against the signal from regional impedance tomography to obtain information about the regional pressure impedance relationship. During mechanical ventilation this information could be used to titrate the appropriate levels of airway pressure (i.e. peak or mean airway pressure or positive end-expiratory pressure) with respect to regional of global lung expansion and ambient, intra-abdominal, intra-thoracic or other pressures. Pressure and impedance signals should be fed into the same device.

In the following, several measures for the improvement of the signal quality will be described. The improvements in the efficiency and performance of the electrodes and the signal transmission will ameliorate the EIT image acquisition in terms of speed and reliability. This will allow obtaining the EIT data in synchrony with the respiratory cycle. The synchronization can be achieved using external ventilator signals, automated plethysmograph signals or with the system's own impedance signals. This is of physiological importance, as it will provide information about the regional lung changes along the respiratory cycle especially at end inspiration and expiration. This way tidal recruitment and de-recruitment of terminal lung (alveoli) within one respiratory cycle can be detected.

Furthermore the EIT image acquisition can also be triggered by or synchronized with the cardiac cycle using the signal from simple ECG electrodes. Regional changes in pulmonary perfusion can thus be analyzed. Furthermore the synchronization with the cardiac cycle will help reduce or eliminate cardiac disturbances of impedance images of the lung; the resolution of respiratory imaging will thus increase.

Today, electrical impedance signals of the thorax are relative signals (they reflect changes but no absolute values) and it has been difficult to convert them into absolute numbers. Using the above mentioned catheters and/or tubes within the thorax it is conceivable that internal reference signals for electrical impedance (i.e. a tissue calibration factor) could be generated by currents that are injected and/or received between two or more of these catheters or tubes.

The circumference of the thorax and therefore the distance between adjacent electrodes changes with breathing. These changes can easily be measured by conventional methods or detected automatically by plethysmographic means. Data reflecting these changes in circumference can be used within the algorithms for image reconstruction, thereby enhancing the quality of the impedance tomographic images. These data can either be inputted continuously or at discrete time intervals.

The quality of the images obtained by impedance tomography alone can be enhanced further if the data from morphometric measurements or anatomical images are superimposed. Ideally, measurements or pictures from computed tomography or magnetic resonance imaging are projected (mathematically, geometrically or literally) on top of the images obtained from impedance measurements. Areas with a certain electrical behavior can thus be seen in relation to their underlying anatomical structures. This way the size of "gray" zones with undetermined morphology and functionality can be reduced (i.e. areas of collapsed lung tissue could be distinguished from the rib cage, from intrapleural fluid or from bone, muscle or fat). Alternatively simple body measurements, (i.e. weight, height, body mass index, circumferences or others) could be used to normalize the mathematical algorithms for impedance image reconstruction.

In the following, an appropriate use of the regional impedance tomography is described to optimize airway pressure application in chronic obstructive pulmonary desease (COPD). In COPD the lung tissue looses its elastic recoil and intrinsic stability. During expiration, small airways collapse if the pressure within them gets lower than a certain threshold pressure. Gas is thus trapped within the lungs. If inspiratory pressures are higher than the pressures required to re-expanding these collapsed airways, gas can move into the terminal parts of the lung and the alveoli. If the inspired amount of gas is larger than the amount that leaves the lung during expiration the lung is gradually expanded until a new steady state at high lung volumes is reached. The way the diseased lug tissue is easily overdistended and is rendered incapable of gas exchange.

In COPD the collapse of airways can be found in one part of the lung and the overdistension of lung units in another. Thus both these pathological situations can found at the same time.

At times, patients with COPD require support of their ventilation by the application of positive (or more infrequently negative) pressure ventilators. If the absolute amount of airway pressure is too high, lung tissue gets overdistended and dysfunctional for gas exchange. If, however, the applied pressures are too low to prevent the collapse of small airways, gas is trapped within the lung without being efficiently exchanged. Often, airway collapse and overdistension coexist within the same lung at a chosen pressure. For an optimal therapeutic result, the best compromise between these two conflicting lung conditions has to be found. Traditional lung mechanics give only a rough estimate of such a compromise. Information about the regional expansion and movement of air is required to approach this comprise.

Regional electrical impedance tomography provides data and images of regional lung ventilation. With increases in airway pressures the gradual emptying of trapped gas can be detected in one area of the lung, whereas other parts of the lung get progressively distended until in the truly overdistended stage no changes in impedance can be detected. By comparing and integrating the quantities of overdistension and emptying of the various portions of the lung at changing airway pressures a best therapeutic "compromise pressure" can be found that reflects optimal lung expansion at minimal pressures.

Furthermore, not only electrodes can be used on the catheters, but only the pressure measurements of the catheters can be used for optimising the accuracy of the regional pressure impedance curves.

We claim:

1. Method for determining the alveolar opening and/or alveolar closing of a lung, comprising the steps of:
    ventilating the lung with an artificial ventilator with inspiratory and expiratory airway pressures,
    measuring according to a method of electrical impedance tomography an impedance signal in a lung zone, and
    changing at least one of the inspiratory and expiratory airway pressures, and
    generating a curve from the measuring step,
    wherein from an observation of the curve of the measured impedance signal a first respiration pressure value is determined at which alveolar closing in said lung zone occurs and/or a second respiration pressure value is determined at which alveolar opening in said lung zone occurs.

2. Method according to claim 1, wherein a first respiration pressure value which corresponds to the alveolar closing of said lung zone is determined as soon as a mean change in the impedance signal based on breathing movements ($A_1$, $A_2$, $A_1'$, $A_2'$) falls below a first breathing movement comparative value and wherein a second respiration pressure value which corresponds to the alveolar opening of said lung zone is determined as soon as the mean change in the impedance signal due to breathing movements ($A_1$, $A_2$, $A_1'$, $A_2'$) moves above a second breathing movement comparative value.

3. Method according to claim 2, wherein based on an expiratory airway pressure with which the lung alveoli are almost open in said lung zone, the expiratory airway pressure is reduced step by step until alveolar closing is determined in said lung zone and wherein based on an expiratory airway pressure with which the alveolar closing was determined, the inspiratory airway pressure is suddenly increased until alveolar opening is determined in said lung zone.

4. Method according to claim 2, wherein the mean change of the impedance signal due to breathing movements ($A_1$, $A_2$, $A_1'$, $A_2'$) is determined based on an averaged mean square root of the impedance signal over a plurality of inspirations.

5. Method according to claim 2, wherein the mean change in the impedance signal due to breathing movements is determined on the basis of an average peak to peak value of the impedance signal over a plurality of inspirations.

6. Method according to claim 2, wherein the first breathing movement comparative value and/or the second breathing movement comparative value are predetermined.

7. Method according to claim 2, wherein the first breathing movement comparative value and/or the second breathing movement comparative value are determined dynamically from the mean change in the impedance signal due to breathing movements in a different lung zone.

8. Method according to claim 7, wherein the different lung zone is a zone which is above the lung zone concerned in the direction of a gravity vector.

9. Method according to claim 1, wherein a first respiration pressure value which corresponds to the alveolar closing of said lung zone is determined as soon as an average change in the impedance signal due to the collapse of the alveoli (B, B') falls below a collapse comparative value and wherein a second respiration pressure value which corresponds to the alveolar opening of said lung zone which corresponds to the alveolar opening of said lung zone is determined as soon as the average change in the impedance signal due to the opening of the alveoli (B, B') moves above an opening comparative value.

10. Method according to claim 9, wherein based on an expiratory airway pressure with which the lung alveoli are almost open in said lung zone, the expiratory airway pressure is reduced step by step until alveolar closing is determined in said lung zone and wherein based on an expiratory airway pressure with which the alveolar closing was determined, the inspiratory airway pressure is suddenly increased until alveolar opening is determined in said lung zone.

11. Method according to claim 9, wherein the average change in the impedance signal due to the collapse or opening of the alveoli (B, B') is determined on the basis of an average gradient of the impedance signal depending on the inspiratory and expiratory airway pressures.

12. Method according to claim 9, wherein the average change in the impedance signal due to the collapse/opening of the alveoli (B, B') is determined on the basis of a straight line adaptation according to the Gauβ compensation calculation.

13. Method according to claim 9, wherein the collapse comparative value and/or the opening comparative value are predetermined.

14. Method according to claim 9, wherein the collapse comparative value and/or the opening comparative value are determined dynamically from the average change in the impedance signal due to the collapse of the alveoli in another lung zone.

15. Method according to claim 14, wherein the another lung zone is a zone which is above the lung zone concerned in the direction of a gravity vector.

16. Method according to claim 1, wherein a first respiration pressure value which corresponds to the alveolar closing of said lung zone is determined as soon as an average response delay in the impedance signal due to respiration pressure changes (C, C') moves above a first respiration comparative value and wherein a second respiration pressure value which corresponds to the alveolar opening of said lung zone is determined as soon as the average response delay in the impedance signal due to respiration pressure changes (C, C') falls below a second respiration comparative value.

17. Method according to claim 16, wherein based on an expiratory airway pressure with which the lung alveoli are almost closed in said lung zone, the inspiratory airway pressure is pulse-shaped increased until alveolar opening is determined in said lung zone.

18. Method according to claim 16, wherein the average response delay due to respiration pressure changes (C, C') is determined on the basis of an average initial gradient with which the impedance signal follows a change in inspiratory airway pressure.

19. Method according to claim 16, wherein the average response delay due to respiration pressure changes (C, C') is determined on the basis of a time constant with which the impedance signal follows a change in inspiratory airway pressure.

20. Method according to claim 16, wherein the first respiration comparative value and/or the second respiration comparative value are prescribed.

21. Method according to claim 16, wherein the first respiration comparative value and/or the second respiration comparative value are determined dynamically from the average response delay in the impedance signal due to a change of the inspiratory airway pressure in another lung zone.

22. Method according to claim 21, wherein the another lung zone is a zone which is above the lung zone concerned in the direction of a gravity vector.

23. Method according to claim 1, wherein the lung is subdivided into a plurality of zone planes in the direction of a gravity vector.

24. Method according to claim 1, wherein the lung is divided into a plurality of radial sectors, wherein a centre point axis of the sectors is located in the direction of a gravity vector.

* * * * *